United States Patent [19]

Stern et al.

[11] Patent Number: 5,393,792
[45] Date of Patent: Feb. 28, 1995

[54] HIGH DOSAGE TOPICAL FORMS OF COLLAGENASE

[75] Inventors: Harold Stern, Baldwin Harbor; David Yee, Oceanside, both of N.Y.

[73] Assignee: Advance Biofactures of Curacao, N.V., Brievengat, Netherlands Antilles

[21] Appl. No.: 963,995

[22] Filed: Oct. 29, 1992

Related U.S. Application Data

[63] Continuation-in-part of Ser. No. 795,915, Nov. 20, 1991, abandoned.

[51] Int. Cl.$^6$ .................... A01N 25/12; A61K 47/12; A61K 9/50; A61L 9/06
[52] U.S. Cl. .................... 514/777; 514/785; 424/45; 424/445; 424/499; 424/502
[58] Field of Search ............ 424/401, 78.06, 45, 424/445, 499, 94.67, 502; 514/59, 777, 785; 435/212, 219, 220; 530/813, 825; 536/112

[56] References Cited

U.S. PATENT DOCUMENTS

| | | | |
|---|---|---|---|
| 3,392,161 | 2/1974 | Fox | 424/94 |
| 3,678,158 | 7/1972 | Sussman | 424/94 |
| 3,705,083 | 12/1972 | Chiulli et al. | 424/94 |
| 3,876,501 | 4/1975 | Hanushewsky | 530/813 |
| 4,174,389 | 11/1979 | Cope | 424/94 |
| 4,338,300 | 7/1982 | Gelbard | 424/94 |
| 4,485,088 | 11/1984 | Chrapil | 424/304 |
| 4,524,065 | 6/1985 | Pinnell | 424/94 |
| 5,173,295 | 10/1990 | Wehling | 424/94 |

FOREIGN PATENT DOCUMENTS

| | | |
|---|---|---|
| 0312208 | 4/1989 | European Pat. Off. |
| 479615 | 4/1992 | European Pat. Off. |
| 2150833 | 7/1985 | United Kingdom |

OTHER PUBLICATIONS

Mazurek, I. "Report on the Clinical Investigation of Collagenase Ointment in Germany." *Clinical Results in Germany,* 171–175.

Zimmerman, W. E. "The Importance of Collagenase for the . . ." 131–141.

Harper, E. "Collagenases." *Ann. Rev. Biochem.* 1980 49:1063–78.

*Primary Examiner*—G. S. Kishore
*Assistant Examiner*—Carlos Azpuru
*Attorney, Agent, or Firm*—Roland Plottel

[57] ABSTRACT

High concentrations of collagenase as active ingredient in non-aqueous topical pharmaceutical formulations.

11 Claims, 3 Drawing Sheets

HIGH DOSAGE TOPICAL FORMS OF COLLAGENASE

This application is a continuation in part of Ser. No. 07/795,915, filed Nov. 20, 1991, now abandoned, the disclosure of which is hereby incorporated herein by reference.

BACKGROUND OF THE INVENTION

Collagenase ointment has been available in the United States as Collagenase Santyl(R) Ointment (Advance Biofactures Corp., Lynbrook, N.Y. 11563) for 27 years. It has been used on millions of patients. The concentration of collagenase in Santyl(R). Ointment has been no greater than 300 ABC units per gram of ointment. (Collagenase ointment has also been available in other countries.) It is useful for the debridement of burns and of dermal ulcers, particularly bed sores (decubitus ulcers). The debridement of these lesions is necessary to remove dead and dying tissue that is typically a source of microbial infection. In addition, healing does not take place until this necrotic material is removed. Speed of debridement is thus a therapeutic desideratum.

Collagenase ointment has not been so widely accepted by the burn centers in the treatment of third degree burns as perhaps its efficacy deserves. This lack of acceptance is largely due to the perception that third degree burns in particular require a more rapid debridement than the collagenase ointment can provide. A more rapid debridement of severe burns without the necessity for anesthesia or a surgical operation would constitute a therapeutic advancement.

A more rapid debridement would also be useful in the treatment of dermal ulcers since it would provide a superior cost/benefit profile.

SUMMARY OF THE INVENTION

This invention provides pharmaceutical compositions wherein a non-aqueous excipient is mixed with the enzyme collagenase at a collagenase concentration much greater than has heretofore been used in practice, and higher than heretofore mentioned in the literature to our knowledge. These compositions, when used topically to treat burns, ulcers and other wounds, provide rapid debridement of dead and dying tissue without causing undesirable side effects.

Pharmaceutical compositions are prepared by intimately admixing a sterilized collagenase powder with a non-aqueous solid or liquid excipient. Excipients that can be used include (but are not limited to) white petrolatum USP, isopropyl myristate NF, lactose NF, and dextran. In addition, an antibiotic or antiseptic powder such as Polysporin(R) antibiotic, gentamicin, and/or silver sulfadiazine may be added, or may constitute the excipient itself. Polysporin (R) antibiotic powder is a mixture of polymixin B sulfate and bacitracin produced by Burroughs Wellcome.

By non-aqueous excipient is meant a liquid or solid material that is inert towards, i.e., does not significantly affect adversely the physiological activity of, the collagenase, and that is substantially free from water. Water is an undesired constituent. The water or other aqueous solutions of collagenase taught in the literature, if prepared in advance for use, would generally have a safe shelf life at room temperature of not over two weeks.

DETAILED DESCRIPTION

The enzyme collagenase is derived from fermentation by Clostridium histolyticum, and is purified by a chromatographic technique. It possesses the unique ability to digest native and denatured collagen in necrotic tissue.

The potency assay of collagenase is based on the digestion of undenatured collagen (from bovine tendon) at pH 7.2 and 37° C. for 20–24 hours. The number of peptide bonds cleaved are measured by reaction with ninhydrin. Amino groups released by a trypsin digestion control are subtracted. One net ABC unit of collagenase will solubilize ninhydrin reactive material equivalent to 1.09 nanomoles of leucine per minute.

Sterilized collagenase powder is available having a minimum assay of 50 ABC units per mg. The assay may range considerably above that from batch to batch, but is taken into account in determining the weight of powder to admix with excipient to give the desired number of collagenase units per gram of excipient.

The pharmaceutical compositions of this invention contain at least about 1,500 ABC units collagenase per gram of excipient, and preferably range from greater than 2,500 up to 10,000 or more units per gram of excipient. For many applications the concentration will exceed 5,000 units/gram of excipient, e.g., 8,000 units/gram of excipient. In general, within these ranges one should use higher concentrations in powdered or liquid compositions than in ointments, because more of the latter can be applied to, and maintained on, the area to be treated. Preferred ranges for ointments are about 1,500 to about 5,000 and for powders or liquids are about 2,500 to about 10,000 ABC units collagenase per gram of excipient.

Purified collagenase is available as a fine powder, as are most dry excipients. The mixing of dry powders is within the skill of the art, and various kinds of apparatus can be obtained from commercial suppliers. Taking dextran, ordinarily of a molecular weight in the range of about 20,000 to 100,000 daltons, as an example, it is best to mix and package in a controlled atmosphere of low or zero humidity. To avoid oxidation, an inert atmosphere, e.g., nitrogen or helium, can be used.

Rather than mixing dry powders, it is possible to dissolve dextran or other soluble excipient and the collagenase in a solvent, usually water with or without another water soluble solvent such as a lower alcohol, and either precipitate the solutes as by chilling or adding a nonsolvent followed by drying, or spray-dry the solution, or lyophilize the solution, to obtain the dry powdered mixture of collagenase and excipient. Drying of a precipitate followed by grinding, if necessary, should be carried out at near room temperature or lower in a selected atmosphere as described above; likewise spray-drying, which can also advantageously be conducted in vacuo. All such operations are within the skill of the art.

The particle size of final product is not crucial, so long as it dusts or flows easily.

Since dextrans and a number of other powdered excipients absorb moisture easily, our dry powder pharmaceutical compositions should be packaged so as to prevent moisture from entering: therefore, the material from which the package is constructed should be a vapor barrier, and replaceable closures should insure a tight seal.

Packages may take on a number of forms, selected and designed for different needs:

1. Shaker containers, whereby the mixture can be dusted over open surface areas.
2. Aerosol containers (atomizers), whereby the mixture can be sprayed onto or into an affected area by gentle gas or air pulses.
3. Single unit envelopes, which may contain, say, from ½ to 30 grams of the mixture as a single unit dose. Shaker and/or aerosol containers can be fitted with volume controls so that a predetermined quantity (single unit dose) of the powdered mixture is released.

The preparation of ointments by various procedures is within the skill of the art, and various kinds of apparatus can be obtained from commercial suppliers. The high-dosage collagenase ointments of this invention can be packaged in glass jars, squeezable tubes, or in sealed single unit dose envelopes.

The admixture of finely divided solids with nonaqueous liquids is likewise within the skill of the art, as by using high-speed bladed stirrers or other commercially available apparatus. Liquid compositions of this invention can be packaged in bottles, jars, single unit dose envelopes, or preferably aerosol containers which should be well shaken before use to spray onto or into the area to be treated.

It may be desirable to include one or more other medicaments in the collagenase/excipient mixture. Often an antibiotic or antiseptic is added for general prophylaxis against infection and/or to fight infection already present. Other useful additions are anti-inflammatory agents and local anesthetics or analgesics.

For the convenience of the physician, nurse, or other user, a pharmaceutical kit may be sold containing a shaker, spray can, tube or other package containing the pharmaceutical composition of this invention together with a separate shaker or spray can or other package containing an antibiotic in any conventional form. Rather than or in addition to the antibiotic, one can use in a separate package in the kit any medicament intended to reduce infection or to alleviate pain or to induce general healing.

In addition to the non-aqueous excipients mentioned above, further examples of those that may be used are powdered cornstarch, talc. A further example of ointment base is lanolin (caution: allergenic to a small percentage of the population). Suitable liquid excipients are mineral oil, glycerol. Any material proposed for use as an excipient must first be tested in the intended formulation to determine that it is indeed substantially inert towards the collagenase over a considerable length of time, i.e., the desired assured shelf life.

BRIEF DESCRIPTION OF THE DRAWINGS

Chart 1 shows percentage debridement as a function of time, as determined in Experiment Number 1 below, using two different concentrations of collagenase in Polysporin$^{(R)}$, one ten times greater than the other.

Chart 2 shows percentage debridement as a function of time, as determined in Experiment Number 2 below, using two different concentrations of collagenase in petrolatum, one ten times greater than the other.

Figure 1:
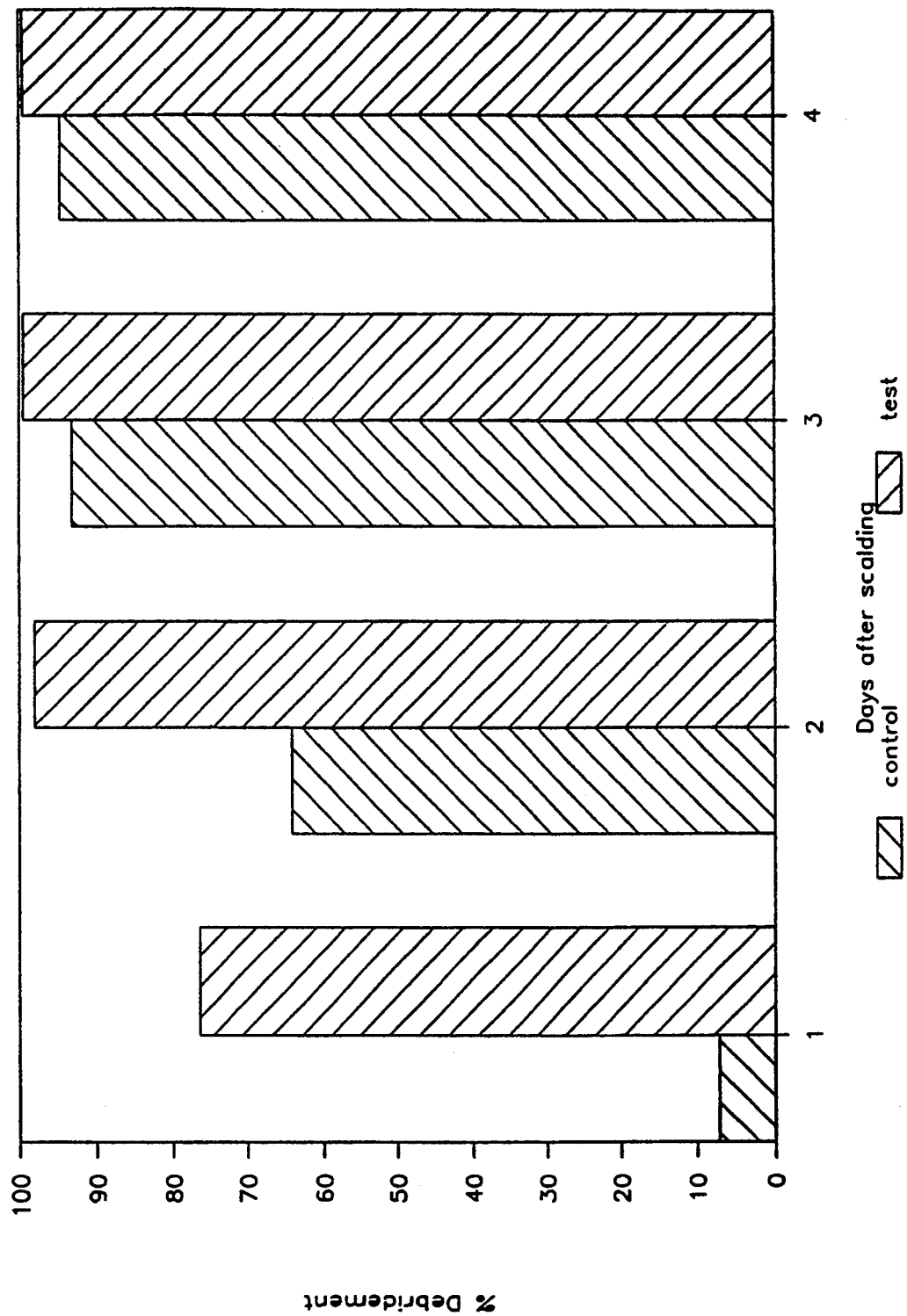
Figure 2:
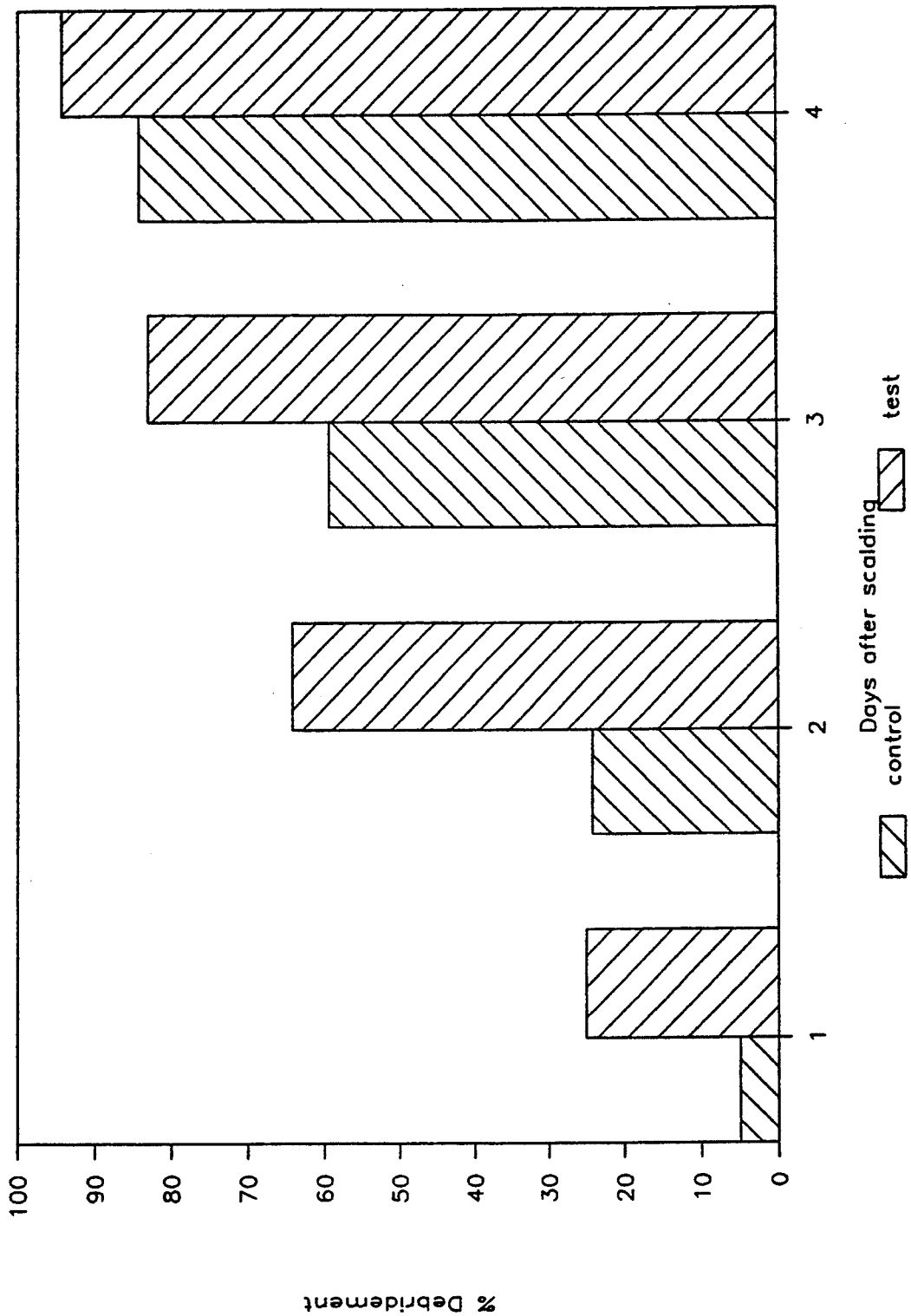
Figure 3:
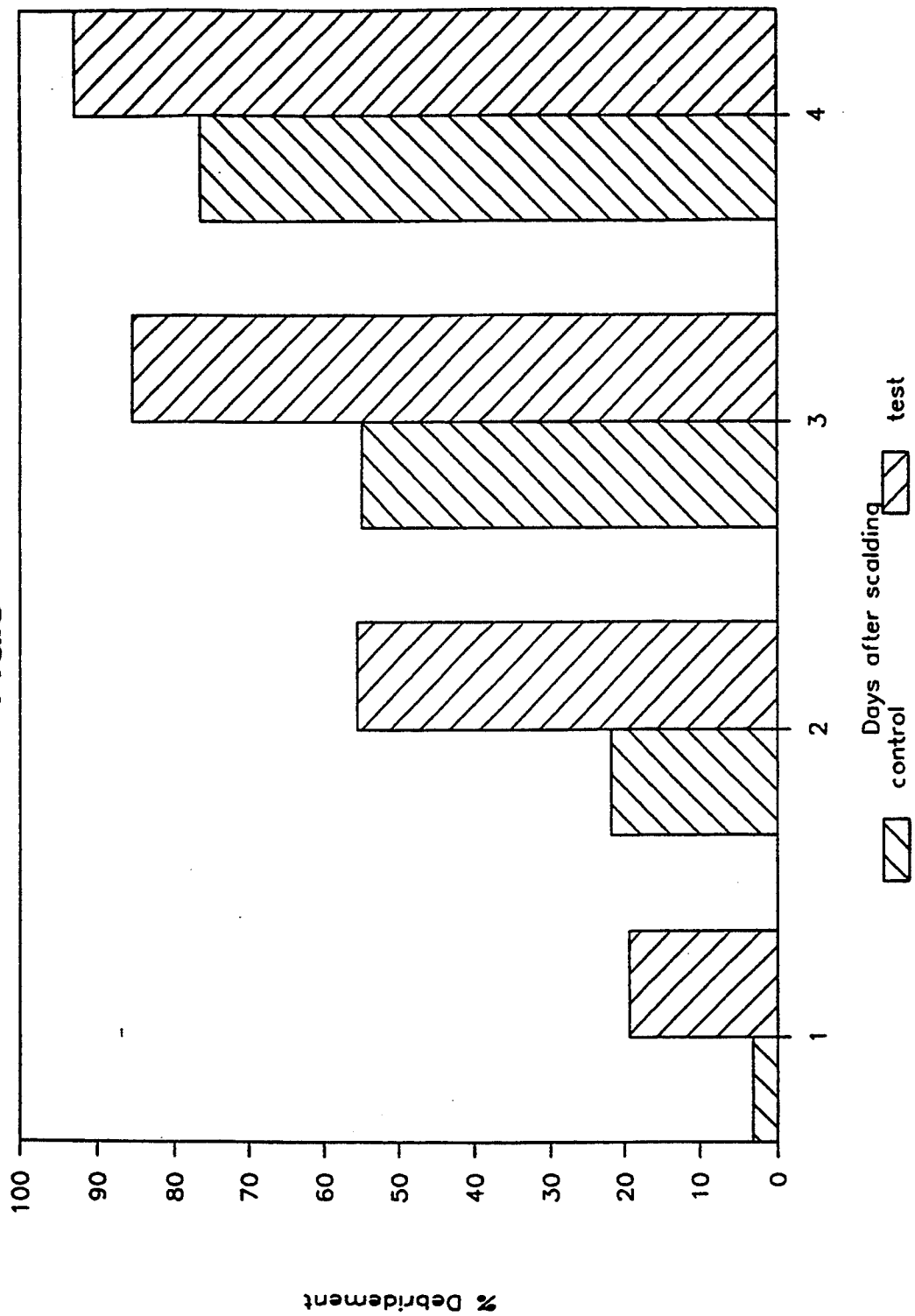

Chart 3 shows percentage debridement as a funciton of time, as determined in Experiment Number 3 below, using two different concentrations of collagenase in lactose NF, one five times greater than the other.

EXAMPLES

Sterile collagenase powder is available from Advance Biofactures Corporation.

White petrolatum USP is commercially available from Witco Chemical.

Polysporin$^{(R)}$ is commercially available from Burroughs Wellcome.

Lactose NF is commercially available from a number of sources, e.g., DMV Campina, Inc.

A number of experiments were carried out to compare the debriding effect of a high-dosage pharmaceutical preparation with a normal dose preparation. In each experiment a number of guinea pigs were anesthetized and were given bilateral third degree burns by being scalded for 20 seconds with a 100-ml beaker containing boiling water. This method produces a well-defined burn and burn eschar of a reproducible size. Some of the burns were treated with the standard amount of collagenase. The other burns were treated with up to ten times the standard amount. All burns were treated with antibiotic. The percentage debridement was assessed by visual inspection and by serial photographic evidence.

The following examples illustrate the difference between standard dose preparations and high-dosage preparations.

Experiment Number 1

Eight guinea pigs were given bilateral third degree burns. Seven of the burns were controls and were treated daily by sprinkling approximately 1 g of Polysporin$^{(R)}$ which contained 800 ABC units of collagenase powder. The lesion was then covered with a 3×3-in sterile gauze pad containing a thin layer of sterile petrolatum. This procedure was repeated for 4 days. The test sides were treated in an identical manner, except that each gram of Polysporin$^{(R)}$ contained 8,000 ABC units of collagenase powder. (The presence of a Polysporin$^{(R)}$-resistant Proteus mirabilis infection necessitated the use of gentamicin powder, which was sprinkled on the wound after treatment with collagenase/-Polysporin$^{(R)}$ but before covering with the gauze pad. Sides 61L, 61R, 62L, 62R, 63L, 63R, 64L, and 64R were treated with gentamicin on the second, third, and fourth days subsequent to burning.)

The results of this experiment are presented in Table 1 and Chart 1. Note that the average percentage debridement with 8,000 ABC units is significantly better (at the 99% degree of confidence, based on the Wilcoxon test) than the debridement seen with 800 ABC units for all four days.

TABLE 1

Percentage Debridement in Experiment Number 1 (Collagenase/Polysporin ®)

| Treatment | Side | Days after scalding | | | |
|---|---|---|---|---|---|
| | | 1 | 2 | 3 | 4 |
| control | 57L | 0 | 20 | 98 | 98 |
| control | 59R | 0 | 75 | 95 | 95 |
| control | 60L | 0 | 20 | 80 | 85 |
| control | 61L | 0 | 75 | 95 | 95 |
| control | 62R | 0 | 90 | 95 | 98 |
| control | 63R | 50 | 90 | 95 | 98 |
| control | 64L | 0 | 80 | 95 | 95 |
| Mean | | 7 | 64 | 93 | 95 |
| test | 57R | 85 | 99 | 99 | 100 |
| test | 58L | 65 | 95 | 100 | 100 |
| test | 58R | 75 | 98 | 100 | 100 |
| test | 59L | 65 | 98 | 100 | 100 |
| test | 60R | 50 | 100 | 100 | 100 |

TABLE 1-continued

Percentage Debridement in Experiment Number 1
(Collagenase/Polysporin ®)

| Treatment | Side | Days after scalding | | | |
|---|---|---|---|---|---|
| | | 1 | 2 | 3 | 4 |
| test | 61R | 98 | 100 | 100 | 100 |
| test | 62L | 80 | 95 | 98 | 98 |
| test | 63L | 75 | 98 | 98 | 98 |
| test | 64R | 95 | 100 | 100 | 100 |
| Mean | | 76 | 98 | 99 | 100 |
| U* | | 0.5 | 0 | 1 | 3 |

*All U values are significant at the 99% degree of confidence (two-tailed test).

Experiment Number 2

Eight guinea pigs were given bilateral third degree burns. Half of the burns were controls and were treated daily by applying a sterile gauze pad containing about 3 g of an ointment of white petrolatum USP containing 270 ABC units of collagenase per gram of petrolatum. This procedure was repeated for 4 days. The test sides were treated in an identical manner, except that the petrolatum used contained 2,700 ABC units of collagenase powder per gram of petrolatum. Gentamicin powder was sprinkled onto the burns of animals 80, 81, 82, and 83 before the collagenase/petrolatum ointment was applied. Similarly, silver sulfadiazine powder was used on animals 86, 87, 88, and 89.

The results of this experiment are presented in Table 2 and Chart 2. Note again that the high-dosage treatment debrided significantly faster than the standard-dose treatment.

TABLE 2

Percentage Debridement in Experiment Number 2
(Collagenase/Petrolatum)

| Treatment | Side | Days after scalding | | | |
|---|---|---|---|---|---|
| | | 1 | 2 | 3 | 4 |
| control | 80R | 0 | 15 | 25 | 70 |
| control | 81L | 0 | 30 | 50 | 85 |
| control | 82R | 0 | 0 | 20 | 65 |
| control | 83L | 0 | 0 | 35 | 40 |
| control | 86L | 10 | 25 | 85 | 98 |
| control | 87R | 5 | 20 | 45 | 65 |
| control | 88L | 5 | 50 | 90 | 98 |
| control | 89R | 5 | 35 | 90 | 90 |
| Mean | | 3 | 22 | 55 | 76 |
| test | 80L | 25 | 50 | 98 | 98 |
| test | 81R | 15 | 70 | 80 | 80 |
| test | 82R | 20 | 65 | 90 | 98 |
| test | 83R | 0 | 30 | 75 | 90 |
| test | 86R | 20 | 30 | 75 | 98 |
| test | 87L | 5 | 50 | 80 | 90 |
| test | 88R | 25 | 65 | 85 | 90 |
| test | 89L | 45 | 85 | 100 | 100 |
| Mean | | 19 | 56 | 85 | 93 |
| U | | 8.5* | 6* | 15.5 | 14.5 |

*significant at the 95% degree of confidence (two-tailed test)

Experiment Number 3

Seven guinea pigs were given bilateral third degree burns. Half of the burns were controls and were treated daily by sprinkling on the wound silver sulfadiazine followed by approximately 1 g of lactose NF that contained 800 ABC units of collagenase powder. The burn was then covered with a 3×3-in sterile gauze pad containing a thin layer of sterile petrolatum. This procedure was repeated for 4 days. The test sides were treated in an identical manner, except that each gram of lactose NF contained 4,000 ABC units of collagenase powder.

The results of this experiment are presented in Table 3 and Chart 3. Note again that the high-dosage treatment debrided significantly faster than the standard-dose treatment.

TABLE 3

Percentage Debridement in Experiment Number 3
(Collagenase/Lactose)

| Treatment | Side | Days after scalding | | | |
|---|---|---|---|---|---|
| | | 1 | 2 | 3 | 4 |
| control | 91L | 30 | 60 | 95 | 95 |
| control | 92R | 0 | 15 | 75 | 95 |
| control | 94L | 5 | 50 | 80 | 95 |
| control | 101L | 0 | 20 | 75 | 90 |
| control | 102R | 0 | 0 | 5 | 50 |
| control | 103L | 0 | 0 | 20 | 85 |
| control | 113R | 0 | 25 | 65 | 80 |
| Mean | | 5 | 24 | 59 | 84 |
| test | 91R | 75 | 85 | 98 | 98 |
| test | 92L | 35 | 65 | 95 | 98 |
| test | 94R | 35 | 85 | 98 | 98 |
| test | 101R | 10 | 50 | 75 | 95 |
| test | 102L | 15 | 60 | 80 | 98 |
| test | 103R | 0 | 35 | 50 | 75 |
| test | 113L | 5 | 70 | 85 | 98 |
| Mean | | 25 | 64 | 83 | 94 |
| U | | 8* | 4* | 11 | 7.5* |

*significant at the 95% degree of confidence (two-tailed test)

We claim:

1. A pharmaceutical composition for topical use consisting essentially of an intimate physical admixture of a non-aqueous excipient and at least about 1,500 ABC units of collagenase per gram of excipient.

2. A composition according to claim 1 in the form of an ointment.

3. A composition according to claim 2 wherein the excipient is petrolatum.

4. A composition according to claim 2 containing from about 1,500 to about 5,000 ABC units of collagenase per gram of excipient.

5. A composition according to claim 1 wherein the excipient is a dry powder.

6. A composition according to claim 5 wherein the excipient is lactose.

7. A composition according to claim 5 wherein the excipient is a mixture of polymixin B sulfate and bacitracin in powder form.

8. A composition according to claim 5 containing from about 2,500 to about 10,000 ABC units of collagenase per gram of excipient.

9. A pharmaceutical composition for topical use consisting essentially of a dry powdered intimate physical admixture of dextran as excipient and in excess of 5,000 ABC units collagenase per gram of dextran.

10. A composition according to claim 5 containing at least about 8,000 ABC units of collagenase per gram of excipient.

11. A composition according to claim 1 that also contains an antibiotic or antiseptic.

* * * * *